United States Patent [19]

Cohn

[11] Patent Number: 4,868,179
[45] Date of Patent: Sep. 19, 1989

[54] METHOD OF REDUCING MORTALITY ASSOCIATED WITH CONGESTIVE HEART FAILURE USING HYDRALAZINE AND ISOSORBIDE DINITRATE

[76] Inventor: Jay N. Cohn, 4848 Russel Av. S., Minneapolis, Minn. 55410

[21] Appl. No.: 41,210

[22] Filed: Apr. 22, 1987

[51] Int. Cl.[4] ...................... A61K 31/34; A61K 31/50
[52] U.S. Cl. ..................................... 514/248; 514/470
[58] Field of Search ................................ 514/248, 470

[56] References Cited

U.S. PATENT DOCUMENTS

| | | | |
|---|---|---|---|
| 3,753,988 | 8/1973 | Rodway et al. | 514/248 |
| 4,361,564 | 11/1982 | Edwards | 514/248 |

FOREIGN PATENT DOCUMENTS

| | | | |
|---|---|---|---|
| 131927 | 1/1985 | European Pat. Off. | 514/470 |
| 105917 | 6/1983 | Japan | 514/470 |

OTHER PUBLICATIONS

The Merck Index–9th ed–item #3144 at p. 419 "Digoxin", (1976).
Massie et al., Am. J. Cardiol., vol. 40, pp. 794–801, (1977).
Pierpont et al., Chest., vol. 73, pp. 8–13, (1978).
"Current Therapy" Conn., (1981).
"Drug Information", ASHP, (1984).
N. A. Awan et al., Am. J. Med., 71, 153, (1981).
K. Chatterjee et al., Ann. Intern. Med., 92, 600, (1980).
W. S. Colucci et al., Am. J. Cardiol., 45, 337, (1980).
D. H. Fitchett et al., Am. J. Cardioil., 44, 303, (1979).
J. A. Franciosa et al., Am. Heart J., 4, 587, (1982).
J. A. Franciosa et al., JAMA, 240, 443, (1978).
C. V. Leier et al., Circulation, 67, 817, (1983).
B. Massie et al., Circuluation, 63, 269, (1981).
J. N. Cohn et al., N. Engl. J. Med., 314, 1547, (1986).

Primary Examiner—Allen J. Robinson
Attorney, Agent, or Firm—Merchant, Gould, Smith, Edell, Welter & Schmidt

[57] ABSTRACT

A method of reducing mortality associated with chronic congestive heart failure in a patient with impaired cardiac function and concomitant reduced exercise tolerance, comprising the oral administration to said patient in need of the same of a combination of (a) between about 75 and about 300 milligrams of hydralazine, per day and (b) between about 40 and about 160 milligrams of isosorbide dinitrate, per day.

2 Claims, No Drawings

METHOD OF REDUCING MORTALITY ASSOCIATED WITH CONGESTIVE HEART FAILURE USING HYDRALAZINE AND ISOSORBIDE DINITRATE

BACKGROUND OF THE INVENTION

The work which resulted in the present invention was supported by the Cooperative Studies Programs of the Medical Research Services, Veterans Administration Central Office, Washington, D.C.

The present invention relates to a method of reducing the incidence of mortality associated with chronic congestive heart failure in patients, by administering to such patients an effective amount of a combination of hydralazine, or a pharmaceutically acceptable salt thereof, and isosorbide dinitrate.

Hydralazine, or 1-hydrazinophthalazine, and the pharmaceutically acceptable acid addition salts thereof is disclosed in U.S. Pat. No. 2,484,029 which issued Oct. 11, 1949. Hydralazine, in the form of its hydrochloride salt, is a widely used arteriolar dilator drug indicated for use in the treatment of essential hypertension. Although hydralazine hydrochloride has been found to exert a sustained hemodynamic effect in patients with chronic congestive heart failure, studies have not confirmed that this drug can increase exercise tolerance or relieve symptoms when given alone, as see Chatterjee et al., *Ann. Intern. Med.*, Vol. 92, pp. 600–604 (1980) and Franciosa et al., *Am. Heart J.*, Vol. 104, pp. 587–594 (1982).

Isosorbide dinitrate, or 1,4:3,6-dianhydrosorbitol 2,5-dinitrate, is a widely used peripheral dilator, producing a vasodilatory effect on both peripheral arteries and veins with predominant effects on the latter. Isosorbide dinitrate is indicated for the treatment and prevention of angina pectoris and may be symptomatically effective in improving the exercise capacity of patients suffering from chronic congestive heart failure, as see C. V. Leier et al., *Circulation*, Vol. 67, pp. 817–822 (1983).

The rationale for vasodilator therapy for heart failure is evidence that vasoconstriction in the systemic arterial and venous beds raises impedance to left ventricular ejection and shifts blood centrally from the venous capacitance vessels. The results of these circulatory effects is increased preload and afterload that adversely affect left ventricular performance and contribute to low cardiac output and venous congestion that characterize heart failure.

The combined use of hydralazine hydrochloride and isosorbide dinitrate has been suggested in the vasodilator therapy of patients with chronic heart failure and for the purpose of eliciting a favorable symptomatic hemodynamic effect on left ventricular performance, as see B. Massie et al., *Am. J. Cardiol.*, Vol. 40, pp. 794–801 (1977) and G. L. Pierpont et al., *Chest*, Vol. 73, pp. 8–13 (1978).

Prazosin hydrochloride, an alpha-adrenoceptor antagonist indicated for the treatment of hypertension, has likewise been suggested in the vasodilator therapy of patients with chronic heart failure and for the purpose of eliciting a favorable symptomatic hemodynamic effect on left ventricular performance, as see N. A. Awan et al., *Am. J. Med.*, Vol. 71, pp. 153–160 (1981) and W. S. Colucci et al., *Am. J. Cardiol.*, Vol. 45, pp. 337–344 (1980).

However, in neither the studies conducted with prazosin hydrochloride, nor the studies conducted with a combination of hydralazine hydrochloride and isosorbide dinitrate, has any influence on mortality been established.

It has now been surprisingly and unexpectedly discovered that while no statistically significant reduction in mortality could be established using prazosin hydrochloride in vasodilator therapy in chronic congestive heart failure, a combination of hydrazaline hydrochloride and isosorbide nitrate has been formed to substantially and significantly reduce the incidence of mortality in such patients.

It is therefor an object of the present invention to provide a method of reducing the incidence of mortality associated with chronic congestive heart failure in patients by orally administering a combination of hydralazine, or a pharmaceutically acceptable salt thereof, and isosorbide dinitrate to such patients in need of the same.

It is a further object of the present invention to provide compositions containing hydralazine or a pharmaceutically acceptable salt thereof, and isosorbide dinitrate for use in such method.

These and other objects of the present invention are apparent from the following detailed disclosures.

DETAILED DESCRIPTION OF THE INVENTION

One embodiment of the present invention relates to a method of reducing mortality associated with chronic congestive heart failure in a patient with impaired cardiac function and concomitant reduced exercise tolerance, comprising the oral administration to said patient in need of the same of a combination of (a) between about 75 and about 300 milligrams of hydralazine or a pharmaceutically acceptable acid addition salt thereof, per day, and (b) between about 40 and about 160 milligrams of isosorbide dinitrate, per day.

By impaired cardiac function in such patient is meant a patient exhibiting abnormal cardiac dilatation, as evidenced, for example, either by a cardiothoracic ratio greater than about 0.55 on a chest X-ray film or by a left ventricular internal diameter diastole greater than about 2.7 centimeter per square meter on echocardiography, or a patient exhibiting left ventricular functional impairment, as evidenced, for example, by a radionuclide ejection fraction less than about 45 percent.

Reduced exercise tolerance in such patient can be assessed by methods known in the art. For example, a convenient assessment can be made by a progressive maximal bicycle-ergometer exercise test taken while expired air is collected continuously to monitor oxygen consumption, with a peak of generally less than about 25 ml per kilogram of patient body weight per minute. Reduced exercise tolerance is measured by patient breathlessness and fatigue.

In a preferred embodiment of the present invention, the patient with chronic congestive heart failure is additionally treated with digitalis, such as digoxin, preferably orally, to achieve a steady state blood serum concentration of the same of at least about 0.7 nanograms per ml, preferably between about 0.7 and about 2.0 nanograms per ml.

Also, in preferred embodiment of the present invention, the patient with chronic congestive heart failure is additionally placed on a regimen of conventional diuretic therapy to manage edema. Depending upon the diuretic employed, potassium chloride may be administered to the patient in order to optimize the fluid balance while avoiding hypokalemic alkalosis. Preferably, the diuretic therapy is achieved by oral administration of the diuretic, and potassium chloride as needed. Suitable conventional diuretics include, for example, thiazides such as chlorothiazide (about 500 to about 2000 mg orally per day), hydrochlorothiazide (about 50 to about 200 mg orally per day), ethacrynic acid (about 50 to about 400 mg orally per day), furosemide (about 40 to about 200 mg, 1, 2 or 3 times per day), spironalactone (about 25 to about 50 mg orally twice to four times per day), or triamterene (about 50 to about 100 mg orally one to four times per day), or conventional combinations thereof. Where potassium therapy is indicated to prevent hypokalemia, the daily ingestion of foods with high potassium content may be sufficient, such as bananas or orange juice, but potassium chloride in liquid or solid form, e.g. between about 20 to 40 milliequivalents potassium chloride two to four times per day, may be necessary.

The hydralazine may be generally administered in the form of its pharmaceutically acceptable acid addition salt, preferably the hydrochloride salt thereof.

The two ingredients, the hydralazine, or pharmaceutically acceptable salt thereof, and the isosorbide dinitrate, may be orally administered together in the form of a combined unit dose form, or separately, as individual dose forms.

The per diem regimen of the hydralazine and isosorbide dinitrate, for oral administration, is conveniently met, for example, by administering the hydralazine in a unit dose form of a 37.5 milligram capsule orally twice daily up to two such capsules four times daily, and by administering the isosorbide dinitrate as a 20 milligram tablet unit dose form, and orally administering between one-half of such tablet four times a day to two tablets four times a day.

Preferably, therapy is begun by administering 37.5 mg hydrazaline, e.g. in the form of its hydrochloride, four times per day and 20 mg isosorbide dinitrate four times per day. In the absence of side effects, the dosage can be increased to 75 mg hydrazaline hydrochloride and 40 mg isosorbide dinitrate, each given four times per day. If drug related side effects occur, the dosage is reduced to 10 mg of isosorbide dinitrate administered four times daily, and 37.5 mg hydrazaline administered twice daily. Where dose reduction occurs, an attempt may be made at a later date to reinstitute a higher dose regimen.

The combination regimen as described above is intended over a long period. Using this regimen a surprising statistically significant reduction in mortality associated with chronic congestive heart failure in such patients can be achieved during the course of administration.

In order to achieve the objective of the invention, the patient suffering from congestive heart failure should advantageously be placed on the combination therapy for a period preferably in excess of six months, more preferably in excess of one year and most preferably in excess of two years.

The following Example is for illustrative purposes only and is not intended to limit the metes and bounds of the present invention.

EXAMPLE

A total of 642 male patients between the ages of 18 and 75, with chronic congestive heart failure, having impaired cardiac function and reduced exercise tolerance and undergoing conventional treatment with digoxin ($>0.7$ ng per milliliter) and diuretics to optimize fluid balance were entered into a double-blind trial of three groups, one group (183 patients) to receive additional treatment with prazosin, one group (186 patients) to receive a combination of hydralazine hydrochloride and isosorbide dinitrate, and one group (273 patients) to receive placebo. The groups continued their regimen of optimal dose of digoxin and diuretic therapy throughout the study. The placebo group also received placebo tablets and placebo capsules taken four times daily. The prazosin group took prazosin hydrochloride capsules, 2.5 mg, and placebo tablets four times daily. The remaining group was given 37.5 mg of hydralazine hydrochloride capsules and 20 mg of isosorbide dinitrate in matching tablets to be taken four times daily. In all groups, therapy began with one capsule and one tablet four times daily. In the absence of side effects, this dose was increased two weeks later to two capsules and two tablets four times daily. If side effects thought to be drug related occurred, the dose was reduced to half a tablet four times daily or to one capsule twice daily. If the dose were reduced, an attempt was made in each case to reinstitute the full dose at a later date. Of the 642 patients in the study, 284 (44.2 percent) had coronary disease and 358 (53.8 percent) had heart failure unrelated to coronary disease. The distribution of base-line variables in the three treatment groups was remarkably similar. In the study, follow-up averaged 2.3 years, with a range of 6 months to 5.7 years. During the follow-up period, there were 120 deaths in the placebo group (44.0 percent), 91 deaths in the prazosin group (49.7 percent) and 72 deaths in the hydralazine group (38.7 percent). Among the patients with chronic heart failure who died, it was difficult to exclude the heart condition as a contributing factor to death—even when other serious diseases were present. Therefore, the analysis was confined to mortality from all causes. Of the deaths, 45 percent were classified as "sudden". At one year, the cumulative mortality rate in the group treated with the hydralazine-nitrate combination (12.1 percent) was 38 percent lower than in the placebo group (19.5 percent). For mortality by two years, the risk reduction among patients treated with the hydralazine-nitrate combination was 34 percent ($P<0.028$). The cumulative mortality rates at two years were 25.6 percent in the hydralazine-isosorbide dinitrate group and 34.3 percent in the placebo group. At three years, the mortality rate was 36.2 percent in the hydralazine-isosorbide dinitrate group and 46.9 percent in the placebo group. The mortality-risk reduction in the hydralazine-isosorbide dinitrate group was 36 percent vis-a-vis the placebo group after three years. In contrast, over the three year period, the mortality rate in the prazosin group was essentially the same as in the placebo group. Other specifics of this study, including comparative base line data, drop-out analyses, cumulative mortality specifics, and hemodynamic variables in the treatment groups are set forth in Cohn et al., *N. Engl. J. Med.*, Vol. 314, pages 1547–62 (June 1986), the disclosure of which is incorporated herein by reference.

What is claimed is:

1. A method of reducing the incidence of mortality associated with chronic congestive heart failure in a patient with impaired cardiac function and concomitant reduced exercise tolerance, comprising the oral administration to said patient in need of the same of a combination of (a) between about 75 and about 300 milligrams of hydralazine, or a pharmaceutically acceptable acid addition salt thereof, per day, and
(b) between about 40 and about 160 milligrams of isosorbide dinitrate, per day.

2. A method according to claim 1, wherein said patient is further treated orally with digoxin in an amount sufficient to achieve in said patient a blood serum concentration of digoxin of at least about 0.7 nanograms per milliliter and an effective edema managing amount of a pharmaceutically acceptable diuretic selected from the group consisting of thiazides, ethacrynic acid, furosemide, spironalactone and triamterene.

* * * * *